United States Patent [19]

Larock

[11] Patent Number: 5,596,100

[45] Date of Patent: Jan. 21, 1997

[54] PALLADIUM CATALYZED ANNULATION OF INTERNAL ALKYNES

[75] Inventor: Richard C. Larock, Ames, Iowa

[73] Assignee: Iowa State University Research Foundation, Inc., Ames, Iowa

[21] Appl. No.: 416,461

[22] Filed: Apr. 4, 1995

[51] Int. Cl.[6] ............... C07D 217/00; C07D 307/77; C07D 311/02

[52] U.S. Cl. ............ 546/146; 546/14; 546/139; 549/214; 549/396; 549/399; 549/400; 549/405; 549/406; 549/462; 549/466; 549/468; 549/469; 560/8; 564/441

[58] Field of Search ............... 546/14, 139, 146; 549/214, 356, 429, 396, 399, 400, 405, 406, 462, 466, 468, 469; 560/8; 564/441

[56] References Cited

U.S. PATENT DOCUMENTS 4,335,054  6/1982  Blaser et al. ............... 260/465

OTHER PUBLICATIONS

Castro, C. E., et al., "Indoles, Benzofurans, Phthalides, and Tolanes via Copper(I) Acetylides," *J. Org. Chem.* 1966, 31, pp. 4071–4078.

Korte, D. E., et al., "Synthesis of Isocoumarins, Dihydroisocoumarins, and Isoquinolones via π–Allylnickel Halide and π–Olefin–Palladium Complexes," *J. Org. Chem.* 1977, 42, 1329–1336.

Mori, M., et al., "Reactions and Syntheses with Organometallic Compounds. 7. Synthesis of Benzolactams by Palladuim–Catalyzed Amidation," *J. Org. Chem.* 1977, 43, 1684–1687.

Maitlis, P. M., et al., "Acetylenes, Cyclobutadienes and Palladuim: A Personal View," *J. Organomet. Chem.* 1980, 200, 161–176.

Sakamoto, T., et al., "Condensed Heteroaromatic Ring Systems. VIII. Synthesis of 3–Substituted Isocoumarins from o–Halobenzoic Acid Derivatives," *Chem. Pharm. Bull.* 1986, 34, pp. 2754–2759.

Arcadi, A., et al., "Palladium–Catalyzed Reaction of 2–Hydroxyaryl and Hydroxyheteroaryl Halides with 1–Alkynes: An Improvemed Route to the Benzo[b]furan Ring System," *Synthesis*, 1986, pp. 749–751.

Maassarani, F., et al., "Controlled Synthesis of Heterocyclic Compounds through Ring Enlargement by Alkyne Insertions into the Pd–C Bonds of Cyclopalladated Amines Followed by Subsequent Ring Closure," *Organometallics* 1987, 6, pp. 2029–2043.

Sakamoto, T., et al., "Condensed Heteroaromatic Ring Systems. XV.[1)] Synthesis of Pyranopyridinones from Halopyridinecarbonitriles" *Chem. Pharm. Bull.* 1988, 36, 1890–1894.

Schore, N. E., "Transition–Metal–Mediated Cycloaddition Reactions of Alkynes in Organic Synthesis," *Chem. Rev.* 1988, 88, pp. 1081–1119.

Tao, W., et al., "Alkyne Reactions with Arylpalladuim Compounds," *Organometallics*, 1989, 8, 2550–2559.

Larock, Richard C., "New Applications of Organopalladium Compounds in Organic Synthesis," *Pure & Appl. Chem.*, 1990, 62, pp. 653–660.

Larock, R. C., et al., "Synthesis of Indoles via Palladuim–Catalyzed Heteroannulation of Internal Alkynes," *J. Am. Chem. Soc.*, 1991, 113, pp. 6689–6690.

Kundu, N. G., et al., "Palladium–catalysed Heteroannulation of Acetylenic Compounds: a Facile Method for the Synthesis of Benzofurans," *J. Chem. Soc. Chem.*, 1992, pp. 41–42.

*Primary Examiner*—Zinna Northington Davis
*Attorney, Agent, or Firm*—Schwegman, Lundberg, Woessner & Kluth, P.A.

[57] ABSTRACT

A method is provided for the regioselective, palladium catalyzed carbo- or heteroannulation of internal alkynes by aryl iodides containing o-substituted side chains to yield aromatic carbocyclic and heterocyclic ring systems.

20 Claims, No Drawings

PALLADIUM CATALYZED ANNULATION OF INTERNAL ALKYNES

The present invention was made with the support of the National Institutes of Health under Grant No. GM40036. The U.S. Government has certain rights in the invention.

BACKGROUND OF THE INVENTION

The transition metal-mediated cycloaddition reactions of alkynes are of great current interest. See, for example, N. E. Schore, *Chem. Rev.*, 88, 1081 (1988). While palladium is among the most widely studied metals for such processes, multiple alkyne insertions, or insertion and subsequent cyclization back on to a preexisting aromatic ring usually predominates. For example, see P. M. Maitlis, *J. Organomet. Chem.*, 200, 1616 (1980). However, a number of groups have recently reported the successful synthesis of fused heterocyclic ring systems employing transition metal catalyses. For example, Larock et al., *J. Amer. Chem. Soc.*, 113, 6689 (1991) have reported the synthesis of various indoles via the palladium-catalyzed heteroannulation of internal alkynes (eq 1):

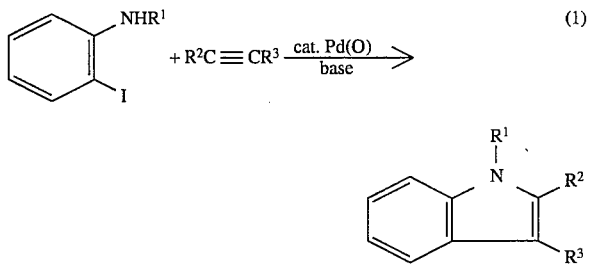

wherein $R^1$ is H, $CH_3$, Ac or Ts, and $R^2$ and $R^3$ are phenyl or alkyl, among others. Synthetic routes to 2-mono-substituted benzofurans via heteroannulation of terminal alkynes have been reported by Castro et al., *J. Org. Chem.*, 31, 4071 (1966); Arcadi et al., *Synthesis*, 749 (1989); and Kundo et al., *J. Chem. Soc., Chem. Commun.*, 41 (1992). Castro et al. did not utilize a palladium catalyst and required the cuprous form of the acetylide (eq. 2). Castro et al. and Kundo et al. also utilized palladium with a copper cocatalyst (eq. 3).

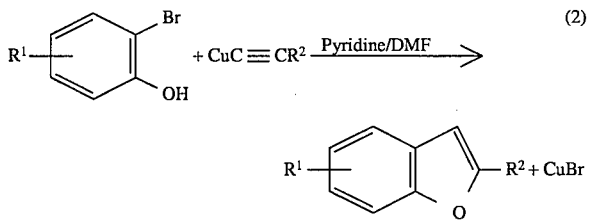

($R^1$ = halo; $R^2$ = phenyl, propyl).

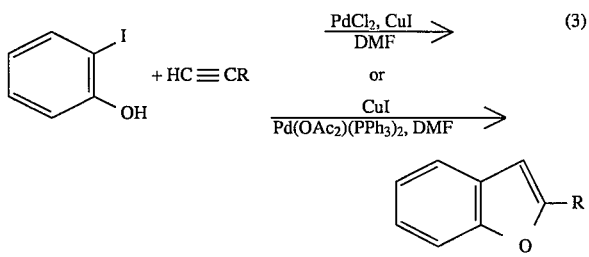

(R = alkyl, hydroxyalkyl).

A single example of Pd-catalyzed carboannulation to yield a 1,1,2,3-tetrasubstituted indene has been reported by R. Larock in *Pure & Appl. Chem.*, 62, 653 (1990).

Therefore, a continuing need exists for effective methods to prepare multi-ring aromatic and heteroaromatic ring systems from relatively simple precursors.

SUMMARY OF THE INVENTION

The present invention provides an efficient, one-step method for preparing fused-ring aromatic compounds, comprising reacting (a) an iodoaryl compound of formula (1):

wherein Y is OH or $C(R^3)(R^4)X$, wherein $R^3$ and $R^4$ are individually H, phenyl or $(C_1-C_4)$alkyl; X is OH, $NO_2$, $CO_2R^5$ $NH_2$ or $NHC(O)R^5$, wherein $R^5$ is aryl or $(C_1-C_4)$alkyl; Ar is a substituted aryl or unsubstituted aryl moiety, and Y and I are positioned adjacent to each other on said moiety; with (b) an internal alkyne of the formula $R^1C\equiv CR^2$ wherein $R^1$ and $R^2$ are individually $(C_1-C_6)$alkyl, aryl, $CO_2R^5$, CHO, $Si(R^3)_3$, 1-methyl(vinyl) or hydroxy$(C_1-C_6)$alkyl; in the presence of effective amount of a Pd catalyst, a base and a chloride ion source, in an organic solvent, to yield a compound of the formula (2):

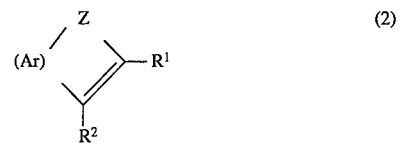

wherein Z is O, $-C(R^3)(R^4)O-$, $-C(R^3)(R^4)N(C(O)R^5)-$, $-CH(CO_2R^5)-$, $-C(R^3)(R^4)NH-$ or $-CH(NO_2)-$; and $R^1-R^5$ are as defined above.

As noted above, Z and I are on adjacent atoms of Ar, i.e., they are ortho in the sense that they are 1,2; 2,3; 3,4, etc. on the ring(s).

A preferred embodiment of formula (1) is a substituted or unsubstituted iodobenzene of the formula (3):

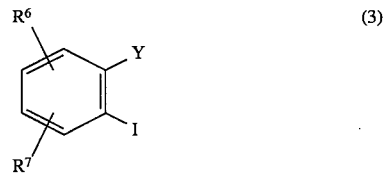

wherein Y is as defined above, and $R^6$ and $R^7$ are individually $(C_1-C_4)$alkyl, chloro, bromo, hydroxy, phenyl, $(C_1-C_4)$alkoxy, $(C_1-C_4)$alkyl(C=O), $(C_1-C_4)$alkoxycarbonyl or together are benzo or methylenedioxy; which, when employed in the present method, yields a compound of the formula (4):

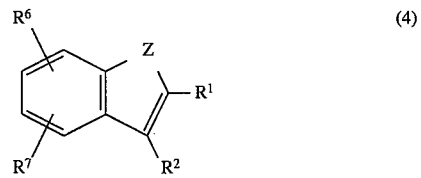

wherein Z, $R^1$, $R^2$, $R^6$ and $R^7$ are as defined above.

Thus, the present invention provides a facile route to a number of aromatic heterocycles and carbocycles from readily available iodobenzenes or iodonaphthalenes, which proceeds in the absence of copper salts or copper catalysts employed by the art with terminal alkynes to form 2-substituted benzofurans. Compounds of formula 2 include 1-nitro or 1-carboalkoxy-indenes (Z=CH(CO$_2$R$^5$) or CH(NO$_2$); 7,8-disubstituted-1,2-dihydroisoquinolines (Z=C(R$^3$)(R$^4$)N(C(O)R$^5$)); 2,3-disubstituted benzofurans (Z=O); and 3,4-disubstituted benzopyrans (Z=C(R$^3$)(R$^4$)O).

These classes of aromatic heterocycles encompass well-known dyes, pharmaceuticals and biocidal compounds such as antimicrobial agents and herbicides, as well as intermediates for the preparation thereof.

Preferably, R.$^3$ and R$^4$ are both H or both CH$_3$, R$^5$ is CH$_3$ or CH$_2$CH$_3$, R$^6$ and R$^7$ are H, (C$_1$–C$_4$)alkyl or acetyl, and R$^1$ and R$^2$ are individually (C$_1$–C$_4$)alkyl, phenyl, CO$_2$(C$_1$–C$_4$)alkyl, CHO or Si((C$_1$–C$_4$)alkyl)$_3$. As used herein, the term "alkyl" includes straight chain alkyl, branched alkyl, cycloalkyl, or (cycloalkyl)alkyl, i.e., methyl, ethyl, isopropyl, t-butyl, cyclopropyl, cyclohexyl, cyclopropylmethyl, and the like. The term "hydroxyalkyl" indicates that the hydroxy group can be at any carbon of the alkyl group.

DETAILED DESCRIPTION OF THE INVENTION

A wide variety of substituted and unsubstituted aryl iodides (ArI) can be employed as starting materials in the present process, and the Ar ("aryl") or R$^2$- or R$^5$-aryl moieties in compound (2) can likewise be substituted or unsubstituted. Preferably, Ar or aryl is a C$_6$–C$_{10}$ aryl moiety, such as phenyl, naphthyl, 2- or 3- thienyl, 2- or 3- furyl, 2-, 3- or 4-pyridyl and the like. A wide variety of 1–3 non-iodo substituents can be present on the Ar or aryl group, including Ph, Br, Cl, F, formyl, OH, amino, nitro, —CH(OCH$_3$)$_2$, —CH(OEt)$_2$, —CO$_2$R$^5$, —CN, (C$_1$–C$_4$)alkyl, (C$_1$–C$_4$)alkoxy, phenoxy, methylene-dioxy, (C$_1$–C$_4$)alkoxycarbonyl, (C$_1$–C$_4$)alkylcarbonyl, hydroxy(C$_1$–C$_4$)alkyl, (R$^3$)(R$^4$)N and (R$^5$)S—, wherein R$^3$, R$^4$ and R$^5$ is as defined above. Other representative Ar-substituents are given in Blaser et al. (U.S. Pat. No. 4,335,054), the disclosure of which is incorporated by reference herein, at Col. 2, line 19 to Col. 3, line 3. The term "aryl" also includes ar(C$_1$–C$_4$)alkyl, e.g., phenethyl or benzyl. Preferably, Ar or aryl is phenyl (Ph) or is phenyl substituted with (C$_1$–C$_4$)alkoxy, acetyl, 3,4-methylene-dioxy, 3,4,5-(tris)-methoxy, hydroxymethyl and the like.

In fact, the upper limits on the molecular weights of the compound of formula (1) are controlled only by physical or practical considerations, such as the solubility of the starting materials, the cost of the starting materials, the reaction conditions and the like.

The compound which is the source of the catalyst is generally employed in an amount of about 0.001–20 mol-%, preferably 0.1–10 mol-%, based on the compound of formula 1. Useful Pd(0) catalysts include, for example, bis-(dibenzylideneacetone)palladium(0), bis(isonitrile)palladium(0), bis(cyclohexylisonitrile)palladium(0), bis-(isopropylisonitrile)palladium(0), bis-(tert.-butylisonitrile)-palladium(0), bis-(p-tolylisonitrile)palladium(0), and bis-(p-methoxyphenylisonitrile)palladium(0). Other Pd-containing compounds, e.g., Pd(II) compounds, can also be used in the present method. These include PdCl$_2$, palladium(II) carboxylate salts, such as Pd(OAc)$_2$, PdBr$_2$, Pd(CN)$_2$, Pd(NO$_3$)$_2$, PdSO$_4$ and the like. Other Pd catalysts which can be used in the present method include those disclosed in Blaser et al. (U.S. Pat. No. 4,335,054) at Col. 6, line 5 to Col. 7, line 3.

Bases used in the present process can be inorganic or organic bases, which are adequately soluble in the reaction medium. Representative bases are disclosed at Col. 7, lines 8–65 of the Blaser et al. patent. Inorganic bases for use in the present process include Na$_2$CO$_3$, KHCO$_3$, Li$_2$CO$_3$, K$_2$CO$_3$ and NaHCO$_3$. Useful organic bases include sodium or potassium acetate, or trialkylamines, such as triethylamine and diisopropyl(ethyl)amine. Preferably, organic bases are used. The preferred mole ratio of the base to the compound of formula 1 is about 2–3:1.

A source of halide, such as chloride ion, is also preferably used in the present process, in an amount effective to promote the reaction and increase the yield. Organic chloride sources, such as tetra(alkyl)ammonium chlorides, wherein the alkyls can each be about (C$_2$–C$_{12}$)alkyl, are preferred, i.e., (n-Bu)$_4$NCl. Alkali metal halides such as MX, wherein M is Li, Na, or K and X is Cl, Br or I, can also be used. Preferred in the present method are LiCl or tetra-n-butylammonium chloride (n-Bu$_4$NCl). The halide source is preferably used in an equimolar amount or in only a slight excess over the compound of formula 1, (1.1–1.5 equivalents).

In carrying out the synthesis of the compound of formula (2), the aryl iodide (1)1 is preferably combined with an excess of the disubstituted acetylene, e.g., preferably in a mole ratio of about 1:1.1–10, in a suitable organic solvent. The reaction mixture is preferably stirred at about 50°–150° C. for about 8–48 hr under an inert atmosphere. The crude product is extracted, i.e., into ethyl acetate and can be purified by chromatography.

Useful organic solvents include tetrahydrofuran (THF), ethers, glycol ethers, dimethylsulfoxide, dimethylformamide (DMF), acetonitrile, acetamide, dimethylacetamide, and hexamethylphosphoramide, and aqueous combinations of these solvents.

In some cases, addition of catalytic amounts of triphenylphosphine (PPh$_3$) was found to improve the yield of product.

A summary of the examples is presented on Table 1, below.

TABLE I

Palladium-Catalyzed Annulation of Alkynes.[a]

| entry | annulating agent | (equiv) | alkyne (equiv) | chloride source | base (equiv) | PPh$_3$ | temp (°C), time (h) | product(s) | % isolated yield |
|---|---|---|---|---|---|---|---|---|---|
| 1 | 2-iodobenzyl-NHAc | (1) | PhC≡CCO$_2$Et (2) | LiCl | NaOAc (2) | – | 100, 24 | *N-Ac, Ph, EtO$_2$C vinyl product* | 80 |
| 2 | " | (1) | " | LiCl | KOAc (2) | – | 100, 24 | " | 80 |
| 3 | " | (1) | PhC≡CPh (2) | n-Bu$_4$NCl | KOAc (2) | – | 120, 24 | *N-Ac, Ph, Ph vinyl product* | 83 |
| 4 | " | (1) | PhC≡CMe (2) | n-Bu$_4$NCl | KOAc (2) | – | 100, 48 | *N-Ac, Ph, Me vinyl product* | 58 |
| 5 | " | (1) | " | n-Bu$_4$NCl | Na$_2$CO$_3$ (2) | + | 100, 48 | " | 62 |
| 6 | " | (1) | PhC≡CCHO (2) | LiCl | NaOAc (2) | – | 100, 24 | *N-Ac, Ph, CHO vinyl product* | 56 |
| 7 | 2-iodophenol-OH | (1) | t-BuC≡CMe (5) | n-Bu$_4$NCl | Na$_2$CO$_3$ (5) | + | 100, 24 | *benzofuran with t-Bu, Me* | 66 |

TABLE I-continued
Palladium-Catalyzed Annulation of Alkynes.[a]
| entry | annulating agent (equiv) | alkyne (equiv) | chloride source | base (equiv) | PPh3 | temp (°C), time (h) | product(s) | % isolated yield |
|---|---|---|---|---|---|---|---|---|
| 8 | (1) | (1.1) | LiCl | K2CO3 (5) | + | 135, 24 | 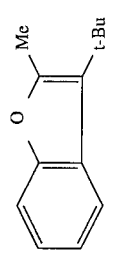 9:1 | 93[b] |
| 9 | (1) | Me<br>H2C=CC≡CEt (1.1) | LiCl | K2CO3 (5) | + | 135, 24 | 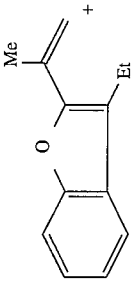 9:1 | 69[b] |
| 10 | (1) | PhC≡CCO2Et (1.1) | LiCl | K2CO3 (5) | + | 135, 24 |  3:2 | 69[b] |

TABLE I-continued

Palladium-Catalyzed Annulation of Alkynes.[a]

| entry | annulating agent | (equiv) | alkyne (equiv) | chloride source | base (equiv) | $PPh_3$ | temp (°C), time (h) | product(s) | % isolated yield |
|---|---|---|---|---|---|---|---|---|---|
| 11 | | (1) | $EtO_2C≡CCO_2Et$ (1.1) | LiCl | $K_2CO_3$ (5) | + | 135, 24 | | 48[b] |
| 12 | | (1.5) | $MeC≡CSi(i-Pr)_3$ (1) | LiCl | $Na_2CO_3$ (1) | − | 100, 72 | | 90 |
| 13 | | (2.8) | $PhC≡CSi(i-Pr)_3$ (1) | LiCl | $Na_2CO_3$ (1) | − | 100, 504 | | 70 |
| 14 | (4-Ac-2-I-phenol) | (1) | $t\text{-}BuC≡CMe$ (5) | $n\text{-}Bu_4NCl$ | KOAc (5) | + | 100, 24 | | 75 |
| 15 | | (1) | $MeC≡CSi(i-Pr)_3$ (2) | LiCl | $Na_2CO_3$ (1) | − | 100, 24 | | 62 |
| 16 | (2-(2-hydroxy-2-propyl)iodobenzene) | (1) | $t\text{-}BuC≡CMe$ (2) | LiCl | $Na_2CO_3$ (2) | − | 100, 20 | 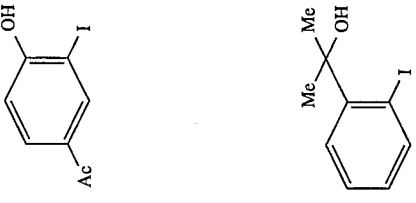 | 52 |

TABLE I-continued

Palladium-Catalyzed Annulation of Alkynes.[a]

| entry | annulating agent | (equiv) | alkyne (equiv) | chloride source | base (equiv) | PPh₃ | temp (°C), time (h) | product(s) | % isolated yield |
|---|---|---|---|---|---|---|---|---|---|
| 17 | CH₂CO₂Et, I (ortho) | (1) | PhC≡CPh (2) | LiCl | Na₂CO₃ (2) | — | 100, 24 | (Me,Me)-C(Me)₂-Ar-C(Ph)=C(Ph)-O... | 52 |
| 18 | CH₂CO₂Et, I (ortho) | (1) | PhC≡CCO₂Et (2) | LiCl | Na₂CO₃ (2) | — | 80, 8 | analogous with CO₂Et | 61 |
| 19 | CH₂CO₂Et, I (ortho) | (1) | PhC≡CCMe₂(OH) (2) | LiCl | Na₂CO₃ (2) | — | 100, 15 | analogous with CMe₂OH | 57 |
| 20 | CO₂Et, I (ortho) | (1) | PhC≡CPh (2) | LiCl | KOAc | — | 100, 48 | indene with CO₂Et, Ph, Ph | 76 |
| 21 | NO₂, I (ortho) | (1) | tBuC≡CMe (5) | LiCl | KOAc | — | 80, 24 | indene with NO₂, tBu, Me | 50 |

TABLE I-continued

Palladium-Catalyzed Annulation of Alkynes.[a]

| entry | annulating agent | (equiv) | alkyne (equiv) | chloride source | base (equiv) | PPh$_3$ | temp (°C), time (h) | product(s) | % isolated yield |
|---|---|---|---|---|---|---|---|---|---|
| 22 | (2-iodobenzyl)NH$_2$ | (1) | PhC≡CCO$_2$Et (2) | LiCl | KOAc | − | 80, 24 | indene with NO$_2$, Ph, Et substituents | 24 |
| 23 | (2-iodobenzyl)NH$_2$ | (1) | n-PrC≡C-n-Pr (3) | LiCl | NaOAc (2) | + | 140, 24 | NH-containing product with n-Pr, n-Pr | 39 |
| 24 | (2-iodobenzyl)OH | (1) | t-BuC≡CMe (2) | LiCl | K$_2$CO$_3$ (2) | − | 100, 48 | O-containing ring with t-Bu, Me | 65 |
| 25 | (2-iodobenzyl)OH | (1) | H$_2$C=C(Me)C≡CEt (2) | LiCl | KOAc (2) | − | 100, 48 | O-containing ring with Me, Et substituents | 50 |

[a]Entries 1–7 were run on a 0.25 mmol scale and entries 8–25 on a 0.50 mmol scale. A representative procedure for the 0.5 mmol scale follows: 5 mol % Pd(OAc)$_2$, aryl iodide (0.5 mmol), n-Bu$_4$NCl or LiCl (0.5 mmol), base (0.5, 1.0 or 2.5 mmol), alkyne (0.5–2.5 mmol), DMF (10 ml), and where necessary (+) 5 mol % PPh$_3$, were placed in a 4 dram vial and heated at the appropriate temperature for the indicated time.
[b]Dimethylacetamide (20 ml) was used as the solvent.
[c]Acetonitrile (10 ml) was used as the solvent.

The experiments initially employed o-iodobenzylamine (entry 23), but annulation with this substrate proved sluggish and even at elevated temperatures only low yields of 1,2-dihydroisoquinolines could be obtained. By employing the corresponding acetamide, instead of the free amine, improved yields were obtained (entries 1–6). Alkynes containing aryl or carbonyl-containing groups gave the best results, and proved highly regioselective.

Heteroannulation using o-iodophenol proved more difficult than analogous reactions of o-iodoaniline (entries 7–13). At the higher temperatures required, reduced regioselectivity is sometimes observed. While the heteroannulation of 4,4-dimethyl-2-pentyne by o-iodophenol (entry 7) at 100° C. gave exclusively 2-t-butyl-3-methylbenzofuran, the analogous, higher-yielding reaction of o-iodophenol run at 135° C. gave a 9:1 mixture of regioisomers (entry 8). The annulation of 2-methyl-1-hexen-3-yne (entry 9) and ethyl phenylpropiolate (entry 10) at 135° C. also afforded mixtures of regioisomers. Hindered silylalkynes give high yields of the corresponding 2-silylbenzofurans (entries 12 and 13). This process complements the copper/palladium-catalyzed coupling of o-iodophenol with terminal alkynes, which affords 2-substituted benzofuran as discussed above, because the silyl-substituted benzofurans are readily desilylated to 3-substituted benzofurans by fluoride salts (eq. 2).

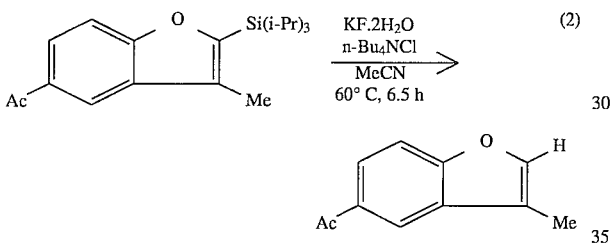

Although alcohols are not particularly good nucleophiles in palladium-based methodology, o-iodobenzylic alcohols have proven effective for the synthesis of benzopyrans (entries 16–19), best results again being obtained using hindered alkyl, aryl or carbonyl-containing alkynes.

Aryl halides bearing an ethoxylcarbonyl group as a carbanion-stabilizing group, such as 2-iodo-phenylacetic acid ethyl ester (entry 20), or 1-nitromethyl-2-iodobenzene (entries 21–22) can also be employed to yield 1substituted indenes.

Although the regiochemistry of every product has not been rigorously established, it appears that generally the aryl group is added to the less hindered end of the alkyne and the palladium moiety to the more hindered end.

The invention will be further described by reference to the following detailed examples.

EXAMPLE 1

General Procedure for the Palladium-Catalyzed Heteroannulation of Alkynes

Palladium acetate (0.0025 mmol), LiCl (0.50 mmol) or n-Bu$_4$Cl (Lancaster, 0.50 mmol), the appropriate base (0.5–2.50 mmol), the aryl iodide (0.50–1.5 mmol), the alkyne (0.5–2.5 mmol), the solvent (10 or 20 ml) and, where indicated, PPh$_3$ (0.025 mmol) were added to a 2 or 4 dram vial equipped with a stirring bar and heated at the appropriate temperature for the necessary period of time. The reaction mixture was diluted with ether, washed successively with saturated NH$_4$Cl and water, dried over anhydrous MgSO$_4$, and concentrated. The products were purified by flash column chromatography. The following compounds were prepared using this general procedure.

A. Ethyl 2-Acetyl-1,2-dihydro-3-phenylisoquinoline-4-carboxylate (entries 1 and 2): $^1$H NMR (CDCl$_3$) δ 0.92 (t, J=7.2 Hz, 3H, CH$_3$), 1.54 (s, 3H, CH$_3$), 4.04 (q, J=7.2 Hz, 2H, CH$_2$), 5.05 (s, 2H, CH$_2$), 7.26–7.60 (m, 8H, aryl), 7.76 (d, J=6.3 Hz, 1H, aryl); $^{13}$C NMR (CDCl$_3$) δ 18.5, 24.5, 40.2, 61.1, 122.2, 123.4, 125.9, 127.7, 128.1, 128.5, 128.7, 129.3, 129.5, 131.9, 140.7, 167.4, 171.2; IR (CDCl$_3$) 1717 (C=O) cm$^{-1}$; HRMS Calcd for C$_{20}$H$_{19}$NO$_3$: 321.1365. Found: 321.1364.

B. 2-Acetyl-1,2-dihydro-3,4-diphenylisoquinoline (entry 3): $^1$H NMR (CDCl$_3$) δ 1.56 (s, 3H, CH$_3$), 5.17 (s, 2H, CH$_2$), 7.09–7.37 (m, 14H, aryl); $^{13}$C NMR (CDCl$_3$) δ 24.0, 46.0, 118.1, 125.0, 125.2, 126.9, 127.2, 127.5, 127.7, 128.1, 129.6, 129.9, 130.7, 132.8, 133.6, 136.3, 136.5, 137.2, 170.1; IR (CDCl$_3$) 1659 (C=O) cm$^{-1}$; HRMS Calcd for C$_{23}$H$_{19}$NO: 325.1467. Found: 325.1458.

C. 2-Acetyl-1,2-dihydro-4-methyl-3-phenylisoquinoline (entries 4 and 5): $^1$H NMR (CDCl$_3$) δ 1.47 (s, 3H, CH$_3$), 2.24 (s, 3H, CH$_3$), 5.00 (s, 2H, CH$_2$), 7.2–7.45 (m, 9H, aryl); $^{13}$C NMR (CDCl$_3$) δ 15.6, 24.1, 45.7, 122.6, 123.6, 123.7, 124.8, 127.3, 127.9, 128.2, 129.9, 133.7, 136.1, 137.6, 137.8, 171.0; IR (CDCl$_3$) 1732 (C=O)cm$^{-1}$; HRMS Calcd for C$_{18}$H$_{17}$NO: 263.1311. Found: 263.1310.

D. 2-Acetyl-,1,2-dihydro-4-formyl-3-phenylisoquinoline (entry 6): $^1$H NMR (CDCl$_3$) δ 1.84 (s, 3H, CH$_3$), 5.12 (s, 2H, CH$_2$), 7.45 (m, 4H, aryl), 7.85 (m, 4 H, aryl), 8.51 (d, J=7.8 Hz, 1H, aryl), 9.75 (s, 1H, CHO); $^{13}$C NMR (CDCl$_3$) δ 24.9, 48.9, 123.4, 124.9, 125.8, 127.7, 128.0, 128.1, 128.9, 131.3, 131.7, 134.0, 140.1, 155.9, 171.1, 190.8; IR (CDCl$_3$) 1736 (C=O) cm$^{-1}$; HRMS Calcd for C$_{18}$H$_{15}$NO$_2$: 277.1103. Found: 277.1101.

E. 2-t-Butyl-3-methylbenzofuran (entries 7 and 8): $^1$H NMR (CDCl$_3$) δ 1.49 (s, 9H, CH$_3$), 2.35 (s, 3H, CH$_3$), 7.25 (m, 2H, aryl), 7.40 (m, 2H, aryl); $^{13}$C NMR (CDCl$_3$) δ 9.0, 29.5, 34.3, 107.3, 110.3, 118.4, 121.7, 123.0, 131.5, 152.8, 159.7; IR (neat) 2961, 1477 cm$^{-1}$; HRMS Calcd for C$_{13}$H$_{16}$O: 188.1204. Found: 188.1201.

F. 3-Ethyl-2-isopropenylbenzofuran and 2-ethyl-3-isopropenylbenzofuran (9:1 mixture) (entry 9): $^1$H NMR (CDCl$_3$) δ 1.21 (t, J=7.5 Hz, 3H, CH$_3$), 2.14 (S, 3H, CH$_3$), 2.77 (q, J=7.5 Hz, 2H, CH$_2$), 5.15 (s, 1H, vinyl), 5.44 (s, 1H, vinyl), 7.15 (m, 2H, aryl), 7.33 (d, J=8.1 Hz, 1H, aryl), 7.43 (d, J=8.1 Hz, 1 H, aryl); $^{13}$C NMR (CDCl$_3$) δ 14.6, 17.6, 21.0, 110.8, 115.0, 118.0, 119.3, 122.0, 124.2, 130.0, 134.6, 151.4, 153.4; IR (neat) 2964, 1287 cm$^{-1}$; HRMS Calcd for C$_{13}$H$_{14}$O: 186.1045. Found: 186.1044.

G. Ethyl 2-phenylbenzofuran-3-carboxylate and ethyl 3-phenylbenzofuran-2-carboxylate (3:2 mixture) (entry 10): $^1$H NMR (CDCl$_3$) δ 1.34 (t, J=7.5 Hz, 6H, CH$_3$), 4.34 (q, J=7.5 Hz, 4H, CH$_2$), 7.28 (m, 4H, aryl), 7.42 (m, 10H, aryl), 7.98 (m, 4H, aryl); $^{13}$C NMR (CDCl$_3$) δ 14.2, 14.3, 14.3, 21.0, 60.3, 60.6, 111.0, 122.6, 123.9, 125.1, 127.1, 128.0, 129.5, 129.6, 130.1, 153.7, 160.8, 163.9, 171.1; IR (neat) 1716 (C=O) cm$^{-1}$; HRMS Calcd for C$_{17}$H$_{14}$O: 266.0943. Found: 266.0944.

H. Diethyl benzofuran-2,3-dicarboxylate (entry 11): $^1$H NMR (CDCl$_3$) δ 1.45 (t, J=7.2 Hz, 6H, CH$_3$), 4.48 (q, J=7.2 Hz, 4H, CH$_2$), 7.38 (t, J=7.38 (t, J=7.8 Hz, 1H, aryl), 7.49 (t, J=7.2 Hz, 1H, aryl), 7.59 (d, J=7.8 Hz, 1H, aryl), 7.92 (d, J=7.8 Hz, 1H, aryl); $^{13}$C NMR (CDCl$_3$) δ 14.2, 14.3, 61.6, 62.2, 112.2, 118.2, 122.7, 124.6, 125.4, 127.9, 145.6, 154.0, 158.8, 162.5; IR (neat) 1726 (C=O) cm$^{-1}$; HRMS Calcd for C$_{14}$H$_{14}$O$_5$: 262.0841. Found: 262.0843.

I. 3-Methyl-2-(triisopropylsilyl)benzofuran (entry 12): $^1$H NMR (CDCl$_3$) δ 1.13 (d, J=7.5 Hz, 18H, CH$_3$), 1.50 (septet, J=7.5 Hz, 3H, CH), 2.33 (s, 3H, CH$_3$), 7.15–7.30 (m, 2H, aryl), 7.44 (d, J=7.8 Hz, 1H, aryl), 7.51 (d, J=6.9 Hz, 1H, aryl); $^{13}$C NMR (CDCl$_3$) δ 8.4, 11.6, 18.6, 111.0, 119.0, 121.5, 123.3, 126.3, 129.9, 155.1, 157.6; IR (CHCl$_3$) 2944, 1461 cm$^{-1}$; HRMS Calcd for C$_{18}$H$_{28}$OSi: 288.1909. Found: 288.1908.

J. 3-Phenyl-2-(triisopropylsilyl)benzofuran (entry 13): $^1$H NMR (CDCl$_3$) δ 1.02 (d, J=7.5 Hz, 18H, CH$_3$), 1.29 (septet, J=7.5 Hz, 3H, CH), 7.10–7.60 (m, 9H, aryl); $^{13}$C NMR (CDCl$_3$) δ 11.7, 18.7, 111.1, 120.0, 122.1, 124.3, 127.6, 128.0, 129.5, 130.0, 133.3, 133.7, 156.1, 157.6; IR (CHCl$_3$) 2945, 1463 cm$^{-1}$; HRMS Calcd for C$_{23}$H$_{30}$OSi: 350.2066. Found: 350.2093.

K. 5-Acetyl-2-t-butyl-3-methylbenzofuran (entry 14): $^1$H NMR (CDCl$_3$) δ 1.37 (s, 9H, CH$_3$), 2.27 (s, 3H, CH$_3$), 2.59 (s, 3H, CH$_3$), 7.31 (d, J=8.4 Hz, 1H aryl), 7.79 (dd, J=1.8, 8.4 Hz, 1H, aryl), 7.99 (d, J=1.8 Hz, 1H, aryl); $^{13}$C NMR (CDCl$_3$) δ 8.9, 26.7, 29.4, 34.4, 108.1, 110.2, 119.7, 124.2, 131.7, 131.8, 155.6, 161.5, 197.9; IR (neat) 1688 (C=O) cm$^{-1}$; HRMS Calcd for C$_{15}$H$_{18}$O$_2$: 230.1307. Found: 230.1302.

L. 5-Acetyl-3-methyl-2-(triisopropylsilyl)benzofuran (entry 15): $^1$H NMR (CDCl$_3$) δ 1.13 (d, J=7.5 Hz, 18H, CH$_3$), 1.51 (septet, J=7.5 Hz, 3H, CH), 2.37 (s, 3H, CH$_3$), 2.67 (s, 3H, CH$_3$), 7.45 (d, J=8.7 Hz, 1H, aryl), 7.93 (dd, J =1.8, 8.7 Hz, 1H, aryl), 8.17 (d, J=1.8 Hz, 1H, aryl); $^{13}$C NMR (CDCl$_3$) δ 9.3, 11.5, 18.5, 26.7, 110.8, 120.5, 124.8, 127.0, 130.2, 131.7, 157.5, 160.3, 197.7; IR (CHCl$_3$) 1675 (C=O) cm$^{-1}$; HRMS Calcd for C$_{20}$H$_{30}$O$_2$Si: 330.2051. Found: 330.2012.

M. 3-t-Butyl-1,1-dimethyl-4-methylisochromene (entry 16): $^1$H NMR (CDCl$_3$) δ 1.27 (s, 9H, CH$_3$), 1.52 (s, 6H, CH$_3$), 2.12 (s, 3H, CH$_3$), 7.0–7.3 (m, 4H, aryl); $^{13}$C NMR (CDCl$_3$) δ 13.7, 26.1, 29.0, 36.3, 75.5, 104.0, 120.8, 121.5, 125.6, 127.0, 134.2, 136.8, 155.7; IR (CHCl$_3$) 2921, 1621 cm$^{-1}$; HRMS Calcd for C$_{16}$H$_{22}$O: 230.1671. Found: 230.1674.

N. 1,1-Dimethyl-3,4-diphenylisochromene (entry 17): $^1$H NMR (CDCl$_3$) δ 1.79 (s, 6H, CH$_3$), 6.88 (d, J=7.5 Hz, 1H, aryl), 7.0–7.4 (m, 13H, aryl); $^{13}$C NMR (CDCl$_3$) δ 27.1, 77.6, 115.6, 122.1, 123.5, 126.8, 127.1, 127.4, 127.5, 127.7, 128.5, 128.7, 131.6, 131.9, 135.9, 136.3, 137.0, 148.1; IR (CHCl$_3$) 2918, 1616 cm$^{-1}$; HRMS Calcd for C$_{23}$H$_{20}$O: 312.1514. Found: 312.1523.

O. Ethyl 1,1-dimethyl-3-phenylisochromene-4-carboxylate (entry 18): $^1$H NMR (CDCl$_3$) δ 0.89 (t, J=7.2 Hz, 3H, CH$_3$), 1.74 (s, 6H, CH$_3$), 4.00 (q, J=7.2 Hz, 2H, CH$_2$), 7.1–7.6 (m, 8H, aryl), 7.9 (dd, J=1.2, 7.5 Hz, 1H, aryl); $^{13}$C NMR (CDCl$_3$) δ 13.5, 27.0, 60.4, 79.5, 108.2, 122.2, 122.8, 127.1, 127.5, 127.7, 127.9, 128.4, 129.6, 134.9, 135.6, 157.4, 168.0; IR (CHCl$_3$) 2928, 1708 cm$^{-1}$; HRMS Calcd for C$_{20}$H$_{20}$O$_3$: 308.1412. Found: 308.1419.

P. 1,1-Dimethyl-3-(1-hydroxy-1-methylethyl)-4-phenylisochromene (entry 19): $^1$H NMR (CDCl$_3$) δ 1.28 (s, 6H, CH$_3$). 1.70 (s, 6H, CH$_3$), 2.22 (s, 1H, OH), 6.50 (d, J=7.5 Hz, 1H, aryl), 7.0–7.6 (m, 8H, aryl); $^{13}$C NMR (CDCl$_3$) δ 26.9, 29.3, 72.9, 112.3, 121.8, 123.6, 126.7, 127.1, 127.3, 128.5, 131.3, 132.4, 135.7, 136.9, 153.1; IR (CHCl$_3$) 3500, 2920 cm$^{-1}$; HRMS Calcd for C$_{20}$H$_{22}$O$_2$: 294.1620. Found: 294.1625.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A process of preparing a compound of formula (2):

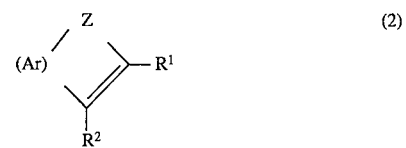

(2)

wherein $R^1$ and $R^2$ are individually (C$_1$–C$_6$)alkyl, (C$_6$–C$_{10}$)aryl, CO$_2$R$^5$, CHO, Si(R$^3$)$_3$, 1-methyl(vinyl) or hydroxy(C$_1$–C$_6$)alkyl; Z is O, —C(R$^3$)(R$^4$)O—, —C(R$^3$)(R$^4$)N(C(O)R$^5$)—, —CH(CO$_2$R$^5$)—, —C(R$^3$)(R$^4$)NH— or —CH(NO$_2$)—; wherein R$^3$ and R$^4$ are individually H, phenyl or (C$_1$–C$_4$)alkyl and R$^5$ is (C$_6$–C$_{10}$)aryl or (C$_1$–C$_4$)alkyl; comprising reacting (a) an iodoaryl compound of formula (1):

(1)

wherein Y is OH or C(R$^3$)(R$^4$)X, and X is OH, NO$_2$, CO$_2$R$^5$, NH$_2$ or NHC(O)R$^5$, wherein R$^5$ is (C$_6$–C$_{10}$)aryl or (C$_1$–C$_4$)alkyl; Ar is a substituted aryl or unsubstituted aryl moiety, and Y and I are positioned adjacent to each other on Ar; with (b) an internal alkyne of the formula R$^1$C≡CR$^2$, in the presence of an effective amount of a Pd catalyst, a base and a chloride ion source, in an organic solvent, to yield said compound of the formula (2).

2. The process of claim 1 wherein Y is OH.

3. The process of claim 1 wherein Y is CH$_2$X or C(CH$_3$)$_2$X.

4. The process of claim 3 wherein X is OH.

5. The process of claim 3 wherein X is NH$_2$ or NHC(O)R$^5$.

6. The process of claim 3 wherein X is CO$_2$R$^5$.

7. The process of claim 1 wherein the palladium catalyst is a Pd(II) compound.

8. The process of claim 7 wherein the Pd(II) catalyst is Pd(OAc)$_2$.

9. The process of claim 1 wherein the base is an alkali metal acetate or carbonate.

10. The process of claim 1 wherein the reaction is carried out at about 50°–150° C. for about 8–48 hrs.

11. The process of claim 1 wherein the reaction is carried out in dimethylformamide or acetonitrile.

12. The process of claim 1 wherein the molar ratio of the compound (1) to the alkyne is about 1:1.1–10.

13. The process of claim 1 wherein the chloride ion source is LiCl.

14. The process of claim 1 wherein the compound of formula 1 is

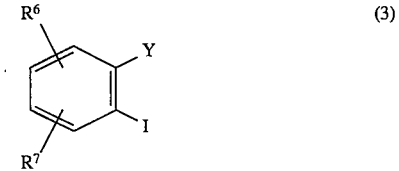

(3)

wherein R$^6$ and R$^7$ are individually (C$_1$–C$_4$)alkyl, chloro, bromo, hydroxy, phenyl, (C$_1$–C$_4$)alkoxy, (C$_1$–C$_4$)alkyl(C=O), (C$_1$–C$_4$)alkoxycarbonyl or together are benzo or methylenedioxy; and the compound of formula (2) is

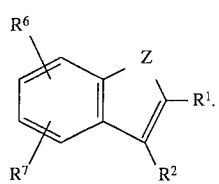

(4)

15. The process of claim 14 wherein Y is OH.
16. The process of claim 14 wherein $R^3$, $R^4$ and $R^5$ are $(C_1-C_4)$alkyl.
17. The process of claim 14 wherein $R^6$ is H.
18. The process of claim 17 wherein $R^7$ is $(C_1-C_4)$alkyl, $(C_1-C_4)$alkoxy or $(C_1-C_4)$alkylC(O).
19. The process of claim 14 wherein $R^1$ and $R^2$ are individually $(C_1-C_4)$alkyl, phenyl, $Si((C_1-C_4)alkyl)_3$ or $CO_2((C_1-C_4)alkyl)$.
20. The process of claim 14 wherein $R^6$ and $R^7$ are H.

* * * * *